United States Patent
De Lacharriere et al.

(10) Patent No.: US 7,537,752 B2
(45) Date of Patent: May 26, 2009

(54) USE OF A COMPOSITION CONTAINING AN EFFECTIVE QUANTITY OF AT LEAST ONE ION CHELATING AGENT FOR INCREASING THE TOLERANCE THRESHOLD OF A SENSITIVE OR INTOLERANT SKIN

(75) Inventors: Olivier De Lacharriere, Paris (FR); Roland Jourdain, Meudon la Foret (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/127,569

(22) Filed: Apr. 23, 2002

(65) Prior Publication Data

US 2003/0026820 A1 Feb. 6, 2003

(30) Foreign Application Priority Data

Apr. 23, 2001 (FR) ................... 01 05457

(51) Int. Cl.
- *A61Q 17/00* (2006.01)
- *A61Q 19/00* (2006.01)
- *A61Q 5/00* (2006.01)

(52) U.S. Cl. .................. 424/70.1; 424/45; 424/401
(58) Field of Classification Search ................. 424/49, 424/401; 514/944
See application file for complete search history.

(56) References Cited

U.S. PATENT DOCUMENTS

| | | | |
|---|---|---|---|
| 5,091,171 A | 2/1992 | Yu et al. | |
| 5,208,013 A | 5/1993 | Klein | |
| 5,876,737 A * | 3/1999 | Schonrock et al. | 424/401 |
| 5,968,532 A * | 10/1999 | De Lacharriere et al. | 424/401 |
| 6,139,850 A | 10/2000 | Hahn et al. | |

FOREIGN PATENT DOCUMENTS

| | | |
|---|---|---|
| DE | 198 45 324 | 4/2000 |
| EP | 0 650 720 | 5/1995 |
| EP | 0 700 896 | 3/1996 |
| EP | 0 856 308 | 8/1998 |
| EP | 0856 308 | 8/1998 |
| WO | WO 90/14833 | 12/1990 |
| WO | WO 95/05852 | 3/1995 |
| WO | WO 97/31620 | 9/1997 |
| WO | WO 98/01110 | 1/1998 |
| WO | WO 99/44579 | 9/1999 |
| WO | WO 99/53892 | 10/1999 |

OTHER PUBLICATIONS

Patent Abstracts of Japan; vol. 2000, No. 08, Oct. 6, 2000 & JP 2000 136122; May 16, 2000.
Database WPI; Section Ch, Week 199814; Derwent Publications Ltd., London, GB; AN 1998-148357 XP0002193650 & JP 10 017493; Jan. 20, 1998, Abstract.
Database WPI; Section Ch, Week 199823; Derwent Publications Ltd.; London, GB; AN 1998-255477 XP002193747 & JP 10 081615; Mar. 31, 1998.
Derwent Abstract of DE 19805827, published Aug. 19, 1999.

* cited by examiner

*Primary Examiner*—Jyothsna A Venkat
(74) *Attorney, Agent, or Firm*—Oblon, Spivak, McClelland, Maier & Neustadt, P.C.

(57) ABSTRACT

Use of a cosmetic and/or dermatological and/or hygiene composition containing an effective quantity of at least one ion chelating agent for increasing the tolerance threshold of sensitive or intolerant skin.

14 Claims, No Drawings

USE OF A COMPOSITION CONTAINING AN EFFECTIVE QUANTITY OF AT LEAST ONE ION CHELATING AGENT FOR INCREASING THE TOLERANCE THRESHOLD OF A SENSITIVE OR INTOLERANT SKIN

The present invention concerns the use of a composition containing an effective quantity of at least one ion chelating agent for treating sensitive or intolerant skins, so as in particular to increase the tolerance threshold of the sensitive or intolerant skin, and also to reduce, or even eliminate, the sensory signs associated with a sensitive or intolerant skin.

In the context of this application, skin should be understood to mean any cutaneous zone of the body, the scalp, or the mucosa (buccal, jugal, gingival and conjonctival) of the human body.

In the context of this application, skin tolerance threshold should be understood to mean the threshold of excitability beyond which the skin reacts to an external attack by a cutaneous hyperreactivity revealed by sensory signs such as stinging, calor, muscle pain, itching, skin discomfort, sometimes combined with red blotching.

External attack also includes irritant products such as the surface-active agents, preservatives, perfumes, soap, hard water with a high calcium concentration, wool, as well as the environment, such as temperature variations and wind, or physical frictions such as shaving rash, excluding allergen substances.

In the field of skin disorders, it is known that the skin reacts to external attack and that some skins react much more quickly to these attacks and are more sensitive or more intolerant than a normal skin.

The mechanisms by which the skin reacts to these attacks were unknown until now. Thus, for example, the process involved in skin sensitivity or intolerance was not clearly understood. Some considered that a sensitive skin was a skin which reacted to cosmetic products, others that it was a skin which reacted to several external factors, not necessarily linked to cosmetic products.

In addition, sensitive or intolerant skins were classed together with allergic skins.

Because the mechanism by which the skin reacted to external attack was not known, it was until now very difficult to anticipate a skin reaction to these attacks and particularly to treat sensitive or intolerant skins. These were thus treated indirectly, for example by limiting the use of irritant products, such as surface-active agents, preservatives or perfumes, in cosmetic compositions.

Some tests had indeed been developed in an attempt to identify sensitive skins, for example the tests with lactic acid and with DMSO which are known to be irritant substances: see for example the article by L. Lammintausta et al., Dermatoses, 1998, 36, pages 45-49, and the article by T. Agner and J. Serup. Clinical and Experimental Dermatology, 1989, 14, pages 214-217.

Unfortunately, these tests did not allow the correct characterization of the mechanisms by which the skin reacted to external attacks, nor to understand those governing sensitive or intolerant skins.

It is now known that the reaction of the skin to external attacks is linked to the excitability of the sensitive cutaneous nerves. It is also known that sensitive or intolerant skins, which are neither inflammations nor allergic skins in so far as no immunological mechanism is involved, respond to external attacks by the same signs as normal skin, but more rapidly and sometimes more violently.

Sensitive or intolerant skins are thus characterized by a group of signs, from which the signs of inflammation such as oedema and those of allergy (always involving an inflammatory reaction, and thus the appearance of oedema) are clearly excluded.

Thus, the French patent application FR-9710853 discloses the use of one or more agonist substances to activate the chlorine and potassium canal receptors of the sensitive nerve fibres of the cutaneous peripheral nervous system for treating sensitive skins. In addition, the French patent application FR-9802783 discloses the use of a compound which inhibits the activity of the sodium and calcium canals of the sensitive nerve fibres of the cutaneous peripheral nervous system in order to increase the tolerance threshold of the skin, and more particularly sensitive or intolerant skin.

The applicant has now discovered that the topical application of a composition containing an effective quantity of at least one ion chelating agent increases the tolerance threshold of sensitive or intolerant skin and thus improves the skin comfort of individuals with sensitive skin.

More particularly, the applicant has found that the topical application of a composition containing an effective quantity of EDTA reduces the cutaneous hyperreactivity of subjects with sensitive skin during the Lactic Acid Stinging Test.

The Lactic Acid Stinging Test is a test for evaluating the cutaneous reactivity of subjects already well defined as having sensitive skin. The Lactic Acid Stinging test consists of applying a solution of lactic acid to an area of skin in the nasal groove, and observing the appearance and intensity of the subjective signs caused by this application, especially stinging.

A person skilled in the art is aware of the use of chelating agents in compositions for topical application to the skin or scalp.

The international application WO-9503032 discloses a composition for topical treatment containing alpha-hydroxy acids (AHA) to improve the appearance of wrinkled, peeling, aged or photo-aged skin. Ion chelating agents, especially of the $Zn^{2+}$ and $Mg^{2+}$ ions, are used to improve the effectiveness of the AHA by a synergetic effect allowing the concentration of the AHA to be reduced. The reduction of the irritation and stinging sensations is linked to the reduction in AHA concentration.

Moreover, the French patent application FR-9802130 discloses a cosmetic composition containing trace elements derived from mineral waters and chelating agents derived from protein hydrolysates of plant origin, used to improve the appearance and condition of the skin, hair and nails, to stimulate cell renewal and combat skin ageing, and for its photoprotective antibacterial, antiviral, antifungal and anti-hair loss activity.

Similarly, the European patent EP-700896 discloses the use of a metal chelating agent in a cosmetic or dermatological composition to protect the skin, hair and mucosa against light and ageing.

Finally, the Japanese patents JP-1049631 and JP-0182407 respectively disclose a moisturizing cosmetic product containing a polymer and a chelating agent to improve dry skin, and a topical composition containing extracts of momordical finctus and an iron chelating agent to prevent inflammation, ageing, and skin darkening, and improve dry skin.

None of these documents concerns a method for increasing the tolerance threshold of sensitive or intolerant skin. In addition, there is no mention of the action of chelating agents to soothe sensitive or intolerant skins.

The object of the invention is thus the use of a cosmetic and/or dermatological and/or hygiene composition containing an effective quantity of at least one ion chelating agent for treating sensitive skins.

Ion chelating agents should be understood to mean chemical or biological (proteins, peptides, etc.) compounds with the capacity to alter and modify the pericellular ionic environment around skin cells by sequestering certain ions, especially the $Na^+$, $K^+$, $Ca^{2+}$ and $Cl^-$ ions.

Examples of chemical chelating agents include:
aminotrimethyl phosphonic acid,
β-alanine diacetic acid,
citric acid,
cyclodextrin,
cyclohexanediamine tetracetic acid,
diethylenetriamine pentamethylene phosphonic acid,
diethanolamine N-acetic acid,
ethylene diamine tetracetic acid (EDTA or $YH_4$) and its sodium ($YH_3Na$, $Y_2H_2Na_2$, $YHNa_3$ and $YNa_4$), potassium ($YH_3K$, $Y_2H_3K_3$ and $YK_4$), calcium disodium, and diammonium salts and its salts with triethanolamine (TEA-EDTA),
etidronic acid,
galactanic acid,
hydroxyethyl ethylenediamine tetracetic acid (HEDTA) and its trisodium salt,
gluconic acid,
glucuronic acid,
nitrilotriacetic acid (NTA) and its trisodium salt,
pentetic acid,
phytic acid,
ribonic acid,
diammonium citrate,
disodium azacycloheptane diphosphonate,
disodium pyrophosphate,
hydroxypropyl cyclodextrin,
methyl cyclodextrin,
pentapotassium triphosphate,
pentasodium aminotrimethylene phosphonate,
pentasodium ethylenediamine tetramethylene phosphonate,
pentasodium pentetate,
pentasodium triphosphate,
potassium citrate,
potassium EDTMP,
sodium EDTMP,
sodium chitosan methylene phosphonate,
sodium hexametaphosphate,
sodium metaphosphate,
potassium polyphosphate,
sodium polyphosphate,
sodium trimetaphosphate,
sodium dihydroxyethylglycinate,
potassium gluconate,
sodium gluconate,
sodium glucopeptate,
sodium glycereth-1 polyphosphate,
tetrapotassium pyrophosphate,
triethanolamine polyphosphate (TEA),
tetrasodium pyrophosphate,
trisodium phosphate,
potassium triphosphonomethylamine oxide,
sodium metasilicate,
sodium phytate,
sodium polydimethylglycinophenolsulfonate,
tetrahydroxyethyl ethylene diamine,
tetrahydroxypropyl ethylene diamine,
tetrapotassium etidronate,
tetrasodium etidronate,
tetrasodium iminodisuccinate,
trisodium ethylenediamine disuccinate,
ethanolamine N,N-diacetic acid,
disodium acetate,
dimercaprol,
deferoxamine,
Zylox, iron chelating agent disclosed and claimed in the international patent application WO 94/61338,
this list being non-limiting.

Examples of biological chelating agents include metallothionein, transferrin, calmodulin, and sodium chitosan methylene phosphonate.

A preferred chemical chelating agent according to the invention is selected from ethylenediamine tetracetic acid (EDTA) and its sodium, potassium, calcium disodium, diammonium, and triethanolamine salts (TEA-EDTA), hydroxyethyl ethylenediamine tetracetic acid (HEDTA) and its trisodium salt, and their mixtures.

The chelating agent is present in the composition used in the method according to the invention in a concentration of from $10^{-6}$ to 10% by weight, preferably from 0.1 to 5% by weight, and more preferably about 2% by weight of the total weight of the composition.

The compositions used in the method according to the invention may additionally contain at least one liquid or solid fatty phase.

In the context of this application, liquid fatty phase should be understood to mean a liquid fatty phase at ambient temperature (25° C.) composed of one or more fatty bodies which are liquid at ambient temperature, also called oils, and are intercompatible.

The oils of the fatty phase of the compositions according to the invention may be polar or non-polar, volatile or non-volatile oils, selected from the oils conventionally used in cosmetics.

The polar oils include the hydrocarbon oils containing ester, ether, acid or alcohol functions or their mixtures, such as for example:

the hydrocarbon oils with a high content of triglycerides consisting of esters of fatty acids and glycerol, of which the fatty acids may have varying chain lengths and may be linear or branched, saturated or unsaturated; these oils particularly include wheat germ, corn, sunflower, and shea, sweet almond, macadamia, apricot, soya, rapeseed, cotton, alfalfa, poppy, pumpkin, sesame, marrow, avocado, hazelnut, grapeseed, blackcurrant, evening primrose, millet, barley, quinoa, olive, rye, safflower, bancoulier, passion flower, rose hip oils and castor oil; or triglycerides of caprylic/capric acids such as those marketed by the Company Stearineries Dubois or those marketed under the trade names Miglyol 810, 812 and 818 by the Company Dynamit Nobel, the synthetic oils of formula $R^1COOR^2$ in which $R^1$ represents a linear or branched higher fatty acid residue, containing from 7 to 19 carbon atoms, and $R^2$ represents a branched hydrocarbon chain containing from 3 to 20 carbon atoms, such as for example Purcellin oil (ketostearyl octanoate), isononyl isononanoate, the alkyl benzoates, the synthetic esters and ethers such as isopropyl myristate, 2ethylhexyl palmitate, the octanoates, decanoates or ricinoleates of alcohols or polyalcohols, the hydroxyl esters such as isostearyl lactate, diisostearyl malate, and the pentaerythritol esters;

the $C_8$ to $C_{26}$ fatty alcohols such as oleic alcohol; and their mixtures.

The apolar oils include the silicone oils which may be volatile or non-volatile, linear or cyclic, liquid at ambient temperature, such as the polydimethylsiloxanes (PDMS) containing alkyl, alkoxy or phenyl groups, which are pendant or at the end of the silicone chain, and have from 2 to 24 carbon atoms; the phenylated silicones, such as the phenyl trimethiocones, the phenyl dimethicones, the phenyl trimethylsiloxy diphenylsiloxanes, the diphenyldimethicones, the diphenyl methyldiphenyl trisiloxanes, the 2-phenylethyl trimethylsiloxysilicates, the hydrocarbons or fluorinated hydrocarbons, which may be linear or branched and of synthetic or inorganic origin, such as the paraffin oils (for example the isoparaffins), and the aliphatic hydrocarbons (for example isododecane), and their derivatives, vaseline, the polydecenes, hydrogenated polyisobutene, such as parleam, squalane, and their mixtures.

In the context of this application, solid fatty phase should be understood to mean a lipophilic fatty compound, solid at ambient temperature (25° C.), with a melting point greater than 40° C. and up to 200° C., in other words a wax.

The waxes are those generally used in the cosmetic or dermatological fields. They are mainly of natural origin such as beeswax, Carnauba, Candellila, Ouricoury or Japanese waxes, cork or sugarcane fibres, paraffin waxes, lignite, microcrystalline waxes, lanolin wax, Montan wax, the ozokerites, the hydrogenated oils such as hydrogenated jojoba oil, but also of synthetic origin such as the polyethylene waxes produced by the polymerization of ethylene, the waxes obtained by the Fischer-Tropsch synthesis, the esters of fatty acids and the glycerides solid at 40° C., the silicone waxes such as the alkyl, alkoxy and/or esters of poly(di)methylsiloxane solid at 40° C.

As is known, the compositions used in the method according to the invention may also contain adjuvants conventionally used in the cosmetic field such as water, optionally thickened or gelified by a thickening agent or a gelling agent of the aqueous phase, essential oils, neutralizing agents, liposoluble polymers, cosmetic or dermatological active ingredients such as for example emollients, moisturizers, vitamins, essential fatty acids, sun filters, emulsifying and co-emulsifying agents, hydrophilic or lipophilic gelling agents, hydrophilic or lipophilic additives, preservatives, antioxidants, solvents, perfumes, fillers, fitters, odour absorbers, colorants and their mixtures.

The quantities of these different adjuvants are those conventionally used in cosmetics, for example from 0.01% to 10% of the total weight of the composition.

These adjuvants, depending on their properties, may be introduced into the fatty phase, the aqueous phase and/or the lipid globules.

Emulsifying agents which may be used in the invention include for example glycerol stearate, polysorbate 60 and the mixture of PEG-6/PEG-32/Glycol Stearate marketed under the trade name Tefose® 63 by the Company Gattefosse.

Solvents which may be used in the invention include the tower alcohols, particularly ethanol, isopropanol and propylene glycol.

Hydrophilic gelling agents which may be used in the invention include the carboxyvinylic polymers (carbomer), the acrylic copolymers such as the copolymers of acrylates/alkyl acrylates, the polyacrylamides, the polysaccharides such as hydroxypropyl-cellulose, the natural gums and the clays.

Lipophilic gelling agents which may be used in the invention include the modified clays such as the bentones, the metal salts of fatty acids such as the aluminium stearates and hydrophobic silica, ethylcellulose, polyethylene.

The compositions used in the method according to the invention may contain other hydrophilic active ingredients such as the proteins or protein hydrolysates, the amino acids, the polyols, urea, allantoin, the sugars and sugar derivatives, the hydrosoluble vitamins, plant extracts and the hydroxyacids.

Lipophilic active ingredients may include retinol (vitamin A) and its derivatives, tocopherol (vitamin E) and its derivatives, the essential fatty acids, the ceramides, the essential oils, salicylic acid and its derivatives.

The compositions used in the method according to the invention may also combine at least one ion chelating agent with other active ingredients specifically intended for the control and/or treatment of skin diseases.

These active ingredients may include for example the agents modifying the differentiation and/or the proliferation and/or the pigmentation of the skin such as retinoic acid and its isomers, retinol and its esters, vitamin D and its derivatives, the oestrogens such as oestradiol, kojic acid or hydroquinone, the antibacterials such as clindamycin phosphate, erythromycin or the antibiotics of the tetracycline class;

the antiparasitics, in particular metronidazole, crotamiton or the pyrethrinoids;

the antifungal agents, in particular the compounds belonging to the imidazole class such econazole, ketoconazole or miconazole or their salts, the polyene compounds, such as amphotericin B, the compounds of the allylamine family such as terbinafine, or octopirox;

the antiviral agents such as acyclovir;

the steroidal anti-inflammatories, such as hydrocortisone, betamethasone valerate or clobetasol propionate, or the non-steroidal anti-inflammatories such as ibuprofene and its salts, diclofenac and its salts, acetylsalticyclic acid, acetaminophene or glycyrrhetinic acid;

the anaesthetics such as lidocaine chlorhydrate and its derivatives;

the antipruritic agents such as thenaldine, trimeprazine or cyproheptadine;

the keratolytic agents such as the alpha- and beta-hydroxycarboxylic or beta-ketocarboxylic acids, their salts, amides or esters and more particularly the hydroxyacids such as glycolic acid, lactic acid, salicylic acid, citric acid and in general the fruit acids, and 5-n-octanoylsalicyclic acid;

the anti-free radical agents, such as alpha-tocopherol or its esters, the dismutase superoxides, certain metal chelating agents or ascorbic acid and its esters;

the anti-seborreics such as progesterone;

the anti-dandruff agents such as octopirox or zinc pyrithione;

the anti-acne agents such as retinoic acid or benzoyl peroxide.

Colorants which may be used in the invention include the lipophilic colorants, the hydrophilic colorants, the pigments and the nacres normally used in cosmetic or dermatological compositions, and their mixtures. This colorant is generally used at a concentration of from 0.01 to 40% of the total weight of the composition, preferably from 5 to 25%.

The liposoluble colorants are, for example, Sudan red, DC Red 17, DC Green 6, carotene, soya oil, Sudan brown, DC Yellow 11, DC Violet 2, DC orange 5, quinoline yellow.

The pigments may be white or coloured, inorganic and/or organic, coated or not.

The inorganic pigments include titanium dioxide, optionally surface-treated, zirconium or cerium oxides, and the iron and chromium oxides, manganese violet, ultramarine blue, chromium hydrate and ferric blue.

The preferred inorganic pigments are the iron oxides, especially red iron oxide, yellow iron oxide, red and yellow iron oxide, brown iron oxide, black iron oxide, and titanium dioxide.

The organic pigments include
carbon black,
the pigments of type D & C, such as D & C Red No 36, and
the lakes based on cochineal carmine, barium, strontium, calcium such as D & C Red No 7 calcium lake, aluminium, such as D & C Red No 27 aluminium lake, D & C Red No 21 aluminium lake, FD & C Yellow No 5 aluminium lake, FD & C Yellow No 6 aluminium lake, D & C Red No 7 and FD & D Blue No 1.

The nacre pigments may be selected from the white nacre pigments, such as mica coated with titanium or bismuth oxychloride, the coloured nacre pigments such as titanium mica with iron oxides, titanium mica with in particular ferric blue or chromium oxide, titanium mica with an organic pigment of the type mentioned above, and the nacre pigments based on bismuth oxychloride.

The compositions used in the method according to the invention may be applied onto the skin (on any part of the body), onto the scalp or onto the mucosa (buccal, jugal, gingival and conjunctival).

Depending on the method of administration, the compositions used in the method according to the invention may be in any pharmaceutical form normally used.

For topical application to the skin, these compositions may be in particular in the form of an aqueous or oily solution or a dispersion of the lotion or serum type, or emulsions of liquid or semi-liquid consistency of the milk type, obtained by dispersion of a fatty phase in an aqueous phase (H/E) or the inverse (E/H), or suspensions or emulsions of soft consistency of the cream type or an aqueous or anhydrous get, or microcapsules or microparticles, or vesicular dispersions of the ionic and/or non-ionic type. These compositions are prepared by the usual methods.

The compositions used in the method according to the invention may also be applied onto the scalp in the form of aqueous, alcoholic or hydro-alcoholic solutions, or in the form of creams, gels, emulsions, foams or in the form of compositions for aerosols additionally containing a propellant agent under pressure.

The quantities of the different constituents in the compositions used in the method according to the invention are those conventionally used in the fields concerned.

The compositions used in the method according to the invention particularly comprise creams for cleansing, protection, treatment or care for the face, hands, feet, the major skin folds, or for the body (for example day creams, night creams, make-up removal creams, foundation creams, sunscreen creams), liquid foundations, cleansing milks, body milks for protection or care, sunscreen milks, lotions, gels or foams for skin care, such as cleansing lotions, sunscreen lotions, artificial tanning lotions, bath compositions, deodorant compositions containing a bactericide, after-shave gels or lotions, depilatory creams, compositions against insect bites, pain-killing compositions, compositions for treating skin disorders such as eczema, rosacea, psoriasis, the lichens, and severe pruritus.

The compositions used in the method according to the invention may also comprise solid preparations comprising cakes of soap or other cleansing products.

The compositions used in the method according to the invention may also be packaged in the form of compositions for aerosols additionally containing a propellant agent under pressure.

The compositions used in the method according to the invention may also be compositions for hair care, and particularly a shampoo, a setting lotion, a treatment lotion, a styling cream or gel, a colouring composition (particularly for oxidation colouring) optionally in the form of a colouring shampoo, conditioning lotions for damaged hair, a permanent wave composition (particularly for the first application of a permanent wave), an anti-hair loss lotion or get, an antiparasite shampoo, etc.

The compositions used in the method according to the invention may also be for bucco-dental use, for example a toothpaste. In this case, the compositions may contain adjuvants and additives normally used in compositions for buccal use, and in particular surface-active agents, thickening agents, humectants, polishing agents such as silica, various active ingredients such as the fluorides, in particular sodium fluoride, and optionally sweetening agents such as sodium saccharinate.

The quantities of the different constituents of the compositions according to the invention are those conventionally used in the fields considered.

The methods according to the invention may in particular be used by applying the hygiene or cosmetic compositions such as those defined above, according to the normal technique for using these compositions. For example: application of creams, gels, serums, lotions, cleansing milks or sunscreen compositions onto the skin or onto dry hair, application of a hair lotion onto wet hair, shampoos, or application of dentifrice onto the gums.

The following examples and compositions illustrate the invention without in any way limiting it. In the compositions, except where otherwise stated, the proportions are percentages by weight.

EXAMPLE

Effect of EDTA on the Skin Reactivity Stimulated by Lactic Acid in Subjects with Sensitive Skin.

A functional in vivo test was performed to demonstrate, on a population with sensitive skin, the palliative effects of pretreatment (monoapplication) of a chelating agent (EDTA) against the stinging sensations induced by application of a lactic acid solution (or Stinger) onto the naso-genial folds.

Subjects
  12 healthy volunteers, of female sex, aged from 18 to 45, of phototype I to IV, with sensitive skin Products
  chelating agent: salt of disodium ethylenediamine tetraacetate (EDTA),
  10% lactic acid solution,
  cosmetic composition according to the invention $CM_1$ containing 2% of EDTA and in the form of a gel.
  cosmetic composition $CM_0$ not containing EDTA (vehicle of $CM_1$) and in the form of a gel.

The compositions $CM_1$ and $CM_0$ are given in table 1 below.

TABLE 1

|  | Composition $CM_1$ | Composition $CM_0$ |
|---|---|---|
| methyl paraben | 0.2% | 0.2% |
| disodium EDTA | 2% | 0% |
| triethanolamine | 0.7% | 0.7% |
| carbomer | 0.7% | 0.7% |
| water | 96.4% | 98.4% |

Methodology

This was a prospective, monocentric, double-blind, randomized study, with the vehicle (composition $CM_0$) as control, with an intra-individual comparison (right naso-genial fold/left naso-genial fold).

The cosmetic composition $CM_0$ was applied at t=0 onto one of the naso-genial folds, and the composition $CM_1$ onto the other naso-genial fold.

A 10% lactic acid solution was applied at t=0 minutes onto the pre-treated areas, one with composition $CM_0$ and the other with composition $CM_1$.

Subsequently, between t=30 minutes and t=35 minutes, the stinging sensations felt by the subject were evaluated using the following scale:
0=no sensation
1=light or doubtful
2=moderate
3=significant Results The results are given in terms of the average stinging score over the whole period, and are shown in table 2.

In order to verify that the results obtained were statistically significant, the hypothesis was established that there was no difference between the respective effects of compositions $CM_1$ and $CM_0$. The probability p that this hypothesis was verified by a Wilcoxon test on the paired data was then calculated. When p was less than or equal to 0.05, the result (average stinging score) was statistically significant.

TABLE 2

|  | Average stinging score ± standard deviation of the mean | value of p* Wilcoxon Test on the paired data | Comparison $CM_1/CM_0$ |
|---|---|---|---|
| $CM_0$ (0% EDTA) | 1.53 ± 0.18 | 0.0234 | reduction of 41% |
| $CM_1$ (2% EDTA) | 0.90 ± 0.1 |  |  |

A statistically significant reduction of the stinging score was observed after a prior application of the cosmetic composition $CM_1$ containing 2% EDTA;

French Patent Application 0105457 filed Apr. 23, 2001, is incorporated herein by reference, as are all documents, references, texts, standards and articles referred to above. Where numerical ranges are noted herein, said ranges include all values and sub-ranges therebetween as if explicitly written out.

The invention claimed is:

1. A method for increasing the tolerance threshold of sensitive or intolerant skin comprising topically applying a composition comprising a tolerance threshold-increasing effective amount of a tolerance threshold-increasing agent consisting of one or more ion chelating agents to the skin of a person in need thereof, wherein the only tolerance threshold-increasing agent(s) present in the composition is one or more ion chelating agents selected from the group consisting of ethylenediamine tetracetic acid (EDTA) and its monosodium, disodium, trisodium, potassium, calcium disodium, diammonium and triethanolamine salts (TEA-EDTA), hydroxylethylethylenediamine tetracetic acid (HEDTA) and its trisodium salt, tetrahydroxyethylenediamine, tetrahydroxypropylethylenediamine, ethylenediamine dissuccinate trisodium salt, and mixtures thereof, said ion chelating agent being present in the composition in an amount of from 0.1 to 5% by weight of the total weight of the composition.

2. The method of claim 1, wherein the composition further comprises at least one liquid or solid fatty phase.

3. The method of claim 2, wherein the composition further comprises a liquid fatty phase comprising at least one oil selected from the group consisting of hydrocarbon oils, plant oils, animal oils, synthetic oils, silicone oils and fluorinated oils.

4. The method of claim 2, wherein the composition further comprises a solid fatty phase comprising at least one wax selected from the group consisting of natural waxes, Carnauba wax, paraffin wax, esters of fatty acids, fatty alcohols and silicone waxes.

5. The method of claim 1, wherein the composition further comprises at least one cosmetic active ingredient.

6. The method of claim 1, wherein the composition further comprises at least one additive selected from the group consisting of water, antioxidants, essential oils, preservatives, neutralizing agents, liposoluble polymers, fillers, perfumes, emulsifying agents, gelling agents, filters, odor absorbers and colorants.

7. The method of claim 1, wherein the composition is in the form of an aqueous or oily solution or dispersion.

8. The method of claim 1, wherein the composition is in the form of an emulsion of liquid or semi-liquid consistency obtained by dispersion of a fatty phase in an aqueous phase or of an aqueous phase in a fatty phase.

9. The method of claim 1, wherein the composition is in the form of a suspension or emulsion of soft consistency.

10. The method of claim 1, wherein the composition is in the form of aqueous, alcoholic or hydroalcoholic solutions suitable for application to the scalp.

11. The method of claim 1, wherein the composition is in the form of a cream, gel, emulsion or foam suitable for application to the scalp.

12. The method of claim 1, wherein the composition is packaged in the form of an aerosol comprising a propellant agent under pressure.

13. The method of claim 1, wherein the ion chelating agent is present in the composition in an amount of about 2% by weight, of the total weight of the composition.

14. The method of claim 1, wherein the ion chelating agent is a chemical chelating agent selected from the group consisting of ethylenediamine tetracetic acid (EDTA) and its monosodium, disodium, trisodium, potassium, calcium disodium, diammonium and triethanolamine salts (TEA-EDTA), hydroxylethylethylenediamine tetracetic acid (HEDTA), tetrahydroxyethylenediamine, tetrahydroxypropylethylenediamine, ethylenediamine dissuccinate trisodium salt, and mixtures thereof.

* * * * *